United States Patent [19]

Goldstein et al.

[11] 4,303,786

[45] Dec. 1, 1981

[54] ISONITRILE DERIVATIVES OF MACROMOLECULES CONTAINING HYDROXYL GROUPS

[75] Inventors: Leon Goldstein, Rehovot; Amihay Freeman, Rishon Lezion; Mordechai Sokolovsky, Tel-Aviv, all of Israel

[73] Assignee: Ramot - Tel-Aviv University, Tel-Aviv, Israel

[21] Appl. No.: 929,229

[22] Filed: Jul. 31, 1978

[30] Foreign Application Priority Data

Aug. 4, 1977 [IL]  Israel ........................................ 52652

[51] Int. Cl.$^3$ .................... C08B 37/02; C08B 11/155; C08B 31/08
[52] U.S. Cl. .................... 536/51; 260/465.6; 260/112.5 R; 435/68; 528/44; 536/18; 536/43; 536/50; 536/53
[58] Field of Search ...................... 536/1, 18, 51, 112, 536/120, 43, 50; 260/465.6

[56] References Cited

U.S. PATENT DOCUMENTS

| | | | |
|---|---|---|---|
| 3,255,253 | 6/1966 | Kuryla | 536/18 |
| 3,298,845 | 1/1967 | Touey et al. | 536/18 |
| 3,883,378 | 5/1975 | Stack | 536/18 |
| 3,900,461 | 8/1975 | Wilson et al. | 536/112 |
| 4,056,672 | 11/1977 | Dahlberg et al. | 536/120 |

FOREIGN PATENT DOCUMENTS

672893  10/1963  Canada ................................ 536/112

*Primary Examiner*—Johnnie R. Brown
*Attorney, Agent, or Firm*—Browdy and Neimark

[57] ABSTRACT

The present invention relates to novel isocyano derivatives of linear or cross-linked, natural or synthetic macromolecules, the derivatives being of the general formula P—O—Q—NC, wherein P is the macromolecular backbone, the oxygen atom is part of the hydroxy group, Q is a group —$(CH_2)_n$—wherein n is an integer of at least 3 carbon atoms, and up to about 20 carbon atoms, or Q is an aralkyl group, to a process for preparing such derivatives and to a process of linking to same biologically active proteins and to the products thus obtained.

11 Claims, No Drawings

ISONITRILE DERIVATIVES OF MACROMOLECULES CONTAINING HYDROXYL GROUPS

FIELD OF THE INVENTION

Novel isocyanide derivatives of polysaccharides and of various polymers having hydroxyl groups, such as polyvinylalcohol, or the like, which isocyanide moieties are attached to the polymer or polysaccharide via stable ether bonds, and a process for the preparation of these. The isocyanides thus prepared are suited for chemically bonding to such polysaccharides or other polymers having hydroxyl groups proteins and other biologically active molecules. Suitable starting materials are the various polysaccharides, and various natural and synthetic or modified polymers containing hydroxyl groups, such as cellulose, starch, linear and cross-linked dextran, linear and cross-linked agarose, various other polysaccharides, N-2-hydroxyethyl derivative of a polyaccyl polymer, polyvinyl alcohol and any other suitable macromolecule subsituted by a plurality of hydroxyl groups. The process of the invention is applicable to solid and liquid macromolecules and the invention relates to all novel isocyano-derivatives of such macromolecules.

BACKGROUND OF THE INVENTION

Chemically bonded biologically active proteins, such as enzymes or the like, which are covalently attached to a suitable polymeric backbone have been described in literature. The covalent bonding of various reactive groups to polymers like cellulose or modified cellulose, and the further bonding of biologically active proteins to such modified products is also known. Bonding was effected via various reactive groups, such as groups attached to the polymeric backbone by reaction with cyanogen bromide, with bromoacetyl bromide etc.

The functional moieties used according to the present invention are of a very versatile nature and it is very easy to obtain various desired products by resorting to easily controlled conditions of reaction.

SUMMARY OF THE INVENTION

The invention relates to novel derivatives of polysaccharides, modified polysaccharides and other polymers having hydroxyl groups, which can be used for covalently bonding biologically active proteins, such as enzymes, antibodies, antigens and the like. The novel polymeric substances contain isocyanide groups bonded to the polymeric backbone via a moiety of adequate size and length so as to prevent cyclizations. The novel isocyanosubstituted polymers can be schematically designates as P—O—Q—NC compounds, where P is the polymeric backbone, Q is a group $(CH_2)_n$— where n is an integer of 3 or more, or Q is araliphatic group, e.g. an aralkyl group. The functional moiety is attached to the polymeric backbone via a chemically stable ether linkage. The isocyanide group is a very versatile group for the covalent bonding of various substances, such as proteins, and especially biologically active proteins, which retain a large percentage of their initial activity. The invention further relates to a novel process for preparing isocyanide derivatives of polysaccharides and other polymers containing hydroxyl groups, which comprises ionizing the hydroxyl groups of the polymer by means of a strong base in a non-aqueous polar aprotic solvent; reacting the ionized polysaccharide or polymer with a compound of the general formula X—Q—NC, wherein X is a good leaving group and Q is as hereinbefore defined. A compound of choice is 3-tosyl-1-isocyanopropane, which is a novel compound, and thus part of the present invention. The solvent of choice is dimethylsulfoxide. The reaction can also be effected in dimethyl formamide and in other similar solvents. The hydroxyl group is advantageously ionized by means of a strong base, such as sodium t-butoxide. Other suitable strong bases, such as isopropoxide, methylsulfinyl carbanion (DMSO$^-$; DMSNa) etc. can also be used. The isocyanide is advantageously first contacted with solid alkali metal hydroxide, such as sodium or potassium hydroxide and the isocyanide is after this reacted with the ionized polymer. Amongst isocyanides which are suitable there may be mentioned 3-tosyl-isocyanopropane. Various other aliphatic or araliphatic isocyanides can be used as well.

The reaction scheme, illustrated with reference to the use of t-butoxide as base and 3-tosyl-1-isocyanopropane is given in the following equation.

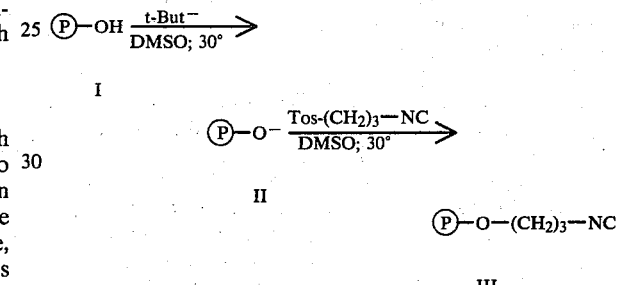

where P designates schematically the polymer which carries a plurality of hydroxyl groups, one of which is shown.

Support for the above reaction scheme was obtained by the synthesis and isolation of a low molecular weight analog of III: $CH_3$—O—$CH_2$—$CH_2$—$CH_2$—NC and its characterization by nmr in deuterated dimethylsulfoxide: $\tau=6.75$ (3H, $CH_3$—O—); $\tau 6.43$ tt; $J_{H-H}=6.2$ HZ, $J_{N-H}=2.1$ Hz (2H, $CH_{2\alpha}$); $\tau=8.15$ m.s.p (2H $CH_{2\beta}$)11$\tau=6.57$ t, $J_{H-H}=6.0$ Hz (2H, $CH_{2\gamma}$).

By this method derivatives of cellulose, cross-linked-dextran (Sephadex), cross-linked-agarose (CL-Sepharose) as well as several linear polyhydroxylic materials, containing isocyanide functional groups were obtained, and used for the covalent bonding of proteins and low molecular weight compounds.

As explained above, the novel compounds of the present invention are of the general formula P—O—Q—NC, where Q is a —$(CH_2)_n$—group and n designates an integer of 3 or more, or an aralkyl group. The integer ought to be at least 3, as otherwise undesired side-reactions take place. The upper limit of n is a matter of convenience, and it is easy to prepare compounds wherein n is an integer between 3 and 20. A preferred range is 3 to about 12. As backbone P there may be used any polymer or macromolecule having a plurality of hydroxyl groups, be this a natural or a synthetic macromolecule. An example of a synthetic macromolecule is a 2-hydroxyethyl substituted polyacrylamide. Other synthetic polymers of similar structure can be used as polymeric support.

The invention is illustrated by way of example only with reference to the following Examples, which are to be construed in a non-limitative manner.

MATERIALS AND METHODS

Sodium t-butoxide was prepared from freshly cut sodium metal and redistilled t-butanol, and diluted in dimethylsulfoxide (1:10) to a final concentration of 0.05 M.

Isocyanide groups were determined titrimetically as described by Freeman et al. (J. Solid Phase Biochem. 1 261, 1977).

Bound protein was determined by total amino acid analysis of acid hydrolyzates of the appropriate enzyme-polymer conjugate. The enzymic activity of trypsin and its insoluble conjugates were determined at 25° by the pH-stat method (Goldstein-Meth. Enzyol. 19 935, 1970).

EXAMPLE 1

Preparation of 3-Tosyl-1-Isocyanopropane 3-tosyl-1-isocyanopropane was prepared from 3-aminopropanol-1 via the N-formylaminopropanol derivative by modification of a procedure described by Matteson and Bailey (J. Am. Chem. Soc. (1968) 90, 3761).

(a) N-formylaminopropanol: An equimolar amount of ethyl formate (264 ml; 0.33 mole) was added dropwise to strongly stirred 3-aminopropane-1-ol (25 ml; 0.33 mole). Stirring was continued for one hour at room temperature. The ethanol formed in the reaction was removed by evaporation at 60° under reduced pressure. The residue was vacuum distilled to yield 26.2 gm (77%) of N-formylaminopropanol (bp 115–118/$\times 10^{-2}$ mm Hg).

(b) 3-tosyl-1-isocyanopropane: A pyridine solution (50 ml) of p-toluene sulfonyl chloride (38.2 gms; 0.2 moles) was added dropwise, in the course of 30 min. to a vigorously stirred ice-cooled solution of N-formyl aminopropanol (10.3 gms; 0.1 mole) in pyridine (50 ml). The reaction mixture was stirred over ice for 1 hr.; 100 ml of cold water were then added and the mixture extracted with three 50 ml portions of ether-hexane 5:1 (V/V). The combined extract was washed with cold water and dried over sodium sulfate. The solvent was removed by evaporation under reduced pressure and the residue redissolved in ether-hexane 3.5:1 (V/V). The solution was left at $-18°$ to induce crystallization. The white crystalline precipitate was separated on a filter and washed with 10 ml of ice-cooled hexane and air-dried. Yield 6–7 gm (25%) mp. 37°-38°. I.R. spectrum in $CHCl_3$: 2155 $cm^{-1}$ (—NC); 1600 $cm^{-1}$ (aromatic ring); 1312, 1125 $cm^{-1}$ (—$SO_2$—); 1455 $cm^{-1}$ (—$CH_3$); 2900 $cm^{-1}$ (—$CH_2$—).

N.M.R. in deuterated dimethylsulfoxide [$(CD_3)_2SO$]: $\tau=2.04$, 2.20, 2.40, 2.55 (4H, Tos); 7.58 (3H $CH_3$-Tos) 6.55 tt; $J_{H-H}=6.0$ Hz $J_{N-H}=3.6$ Hz (a—$CH_2$); 8.06 msp ($\beta$—$CH_2$); 5.8 t, $J_{H-H}=6.0$ Hz ($\gamma$—$CH_2$).

EXAMPLE 2

Preparation of Isocyanide Derivatives of Cellulose

Isocyanide derivatives of cellulose were prepared by a three-step procedure.
(a) preswelling of the polymer,
(b) ionization of polysaccharide hydroxyl groups with t-butoxide and
(c) reacting with 3-tosyl-1-isocyanopropane.

Microcrystalline cellulose powder was suspended with stirring in anhydrous dimethylsulfoxide (15 ml) for 30 min. at 30°. To the swollen powder an 0.05 M solution of sodium t-butoxide in dimethylsulfoxide (10 ml) was added dropwise with stirring. The mixture was stirred for 15 min. to ensure equilibrium ionization of polysaccharide hydroxyl groups.

3-Tosyl-1-Isocyanopropane (480 mg; 2 mole) was dissolved in dimethylsulfoxide (7 ml); the solution was added to a suspension of powdered potassium hydroxide in the same solvent (5 ml) and the mixture stirred vigorously for 10 min. at 30° (to remove acidic impurities). The powder was removed by filtration (glass wool), the filter was washed with 8 ml of dimethyl sulfoxide and the combined filtrate (20 ml total volume) was added to the ionized cellulose-powder suspension.

The reaction was allowed to proceed with stirring for 4 hrs. at 30°. The powder was separated by centrifugation, resuspended in methanol and washed on a filter with 200 ml each of methanol, cold water, methanol ether and air dried. The isocyanide derivative of cellulose (about 40 equiv.$\times 10^{-6}$ NC per gm determined titrimetrically, see Table 1) was stored over Silica gel at $-5°$.

Using different amounts of sodium t-butoxide and 3-tosyl-1-isocyanopropane cellulose derivatives of different isocyanide content could be prepared as summarized in table II.

EXAMPLE 3

Preparation of Isocyanide Derivatives of Cross-Linked Dextrans (Sephadex)

Isocyanide derivatives of the various types of cross-linked dextran (Sephadex) were prepared essentially as described in Example 2 viz. presswelling of the polymer in dimethylsulfoxide and ionization of polysaccharide hydroxyls with sodium t-butoxide, followed by reaction with 3-tosyl-1-isocyanopropane. Since the various types of Sephadex differ in their swelling properties different volumes of dimethylsulfoxide had to be used in the preswelling step.

The amounts of isocyanide had therefore to be adjusted in each case to give the desired final concentration in the reaction mixture. The experimental details for several types of Sephadex are summarized in Table III:

Dry Sephadex beads (1 gm) were suspended in dimethylsulfoxide and left overnight at room temperature (see Table III). The swollen beads were ionized by the addition of 500 equiv. $10^{-6}$ of sodium t-butoxide (10 ml of an 0.05 M solution in dimethyl sulfoxide).

3-Tosyl-1-isocyanopropane was dissolved in dimethylsulfoxide, treated with powdered potassium hydroxide and added to the suspension of ionized Sephadex beads as described in Example 2. (for experimental details see Table III). The reaction was allowed to proceed at 30° for 6 hrs. with slow magnetic stirring.

The modified Sephadex beads were separated on a sintered-glass filter and washed with 200 ml each of methanol, methanol-water (1:1), methanol, ether and air-dried. The isocyanide derivatives of Sephadex were stored over silica gel at $-5°$. The isocyanide content of various preparations (estimated from the leucine content of Sephadex-gly-leu-$NH_2$ conjugates) is given in Tables I and III.

EXAMPLE 4

Preparation of Isocyanide Derivatives of Crosslinked Agarose

Isocyanide derivatives of cross-linked agarose (CL-Sepharose 4B) were prepared as described for cross-linked dextran. The experimental details and isocyanide contents of the various derivatives are given in Tables I and III.

EXAMPLE 5

Preparation of Isocyanide Derivatives of Linear Dextran

Linear dextran of mol. wt. 250,000 (1 gm) was dissolved in dimethylsulfoxide (10 ml). Sodium t-butoxide (10 ml of an 0.05 M solution in dimethylsulfoxide; 500 equiv. $\times 10^{-6}$) was then added dropwise with stirring, and the stirring continued for 15 min. at 30°. 3-Tosyl-1-isocyanopropane (0.54 gm) was dissolved in dimethylsulfoxide (5 ml), and added to a vigorously stirred suspension of powdered potassium hydroxide in diamethylsulfoxide (about 1 gm KOH in 5 ml). Stirring was continued for 10 min. the potassium hydroxide powder was removed by filtration through glass-wool and the filter washed with dimethylsulfoxide (5 ml); the combined filtrate (15 ml) was added to the stirred solution of ionized dextran. The reaction was allowed to proceed with stirring at 30° for 1 hr. The modified polymer was precipitated by the addition of methanol (15 ml) and separated by centrifugation. The pellet was resuspended in dimethylsulfoxide (40 ml) reprecipitated with methanol (20 ml) spinned down and resuspended in methanol (60 ml). The precipitate was then separated by filtration, washed with methanol, ether and air dried. The water-soluble isocyanide derivative of linear dextran (—NC content 50–100 equiv. $\times 10^{-6}$/gm, determined titrimetrically) was stored over silica gel at $-5°$.

EXAMPLE 6

Preparation of Isocyanide Derivatives of Linear Agarose

Isocyanide derivatives of linear agarose were prepared as described for linear dextran. (—NC content about 100 equiv $\times 10^{-6}$/gm, determined titrimetrically).

EXAMPLE 7

Preparation of Isocyanide Derivatives of Polyvinylalcohol

Isocyanide derivatives of linear polyvinylalcohol were prepared as described from linear dextran. (—NC content about 50 equiv $\times 10^{-6}$/gm determined titrimetrically).

EXAMPLE 8

Preparation of Isocyano Derivative of N-2-Hydroxyethyl Substituted Polyacrylamide A linear water-soluble high-molecular weight (i.e. about $10^6$) isocyano-derivative of N-2-hydroxyethyl substituted polyacrylamide was prepared as follows:
a. Polymerization of methylacrylate to form a high molecular weight polymethylacrylate;
b. Reaction of the polymethylacrylate with -aminoethanol in order to convert the ester groups to 2-hydroxyethylamide groups;
c. Introduction of isocyanide groups by the methods set out in Examples 5 to 7.

a. Preparation of high molecular weight polymethylacrylate

To a 500 ml round bottom flask, equipped with a condenser and a magnetic stirrer there were added 160 ml water, 1 g sodium lauryl sulfate, 20 ml of freshly distilled methylacrylate, 20 ml of a stock solution of N,N,N',N'-tetramethyl ethylene diamine (TEMED, 0.46 ml/100 ml), and 280 mg ammonium per sulfate dissolved in 4 ml water. The mixture was stirred magnetically in a water bath at 80° C. for 2 hours. The emulsion was then poured into icecooled water (400 ml) and cold 2 N HCl (400 ml) was added. The white flaky precipitate was washed with cold water, dried and dissolved in acetone (750 ml). The viscous solution was added dropwise into methanol (4 l), the liquid was discarded, and the precipitate resuspended in methanol (250 ml). The liquid was decantated off, and the precipitate resuspended in ether, separated and air dried. Yield: 18 g (94%). The mean molecular weight of the polymer (determined viscosimetrically in benzene) was $1.0.10^6$.

b. Preparation of Poly(N-2-hydroxyethyl)acrylamide 4 g of polymethylacrylate, cut into small pieces, were added to 100 ml of freshly distilled β-aminoethanol and the mixture stirred magnetically at 110° C. for 24 hours. The hot viscous solution was added dropwise to 750 ml propan-2-ol. The precipitate was resuspended in propan-2-ol, the liquid was discarded and the polymer dissolved in cold 0.05 M phosphate buffer pH 6 (100 ml). The pH of the solution was adjusted to 7.0 with concentrated HCl and the solution dialyzed against water at 4° C. and freeze dried. Nitrogen analysis by the Dumas combustion method (N[theoretical]=12.1%, N[found]=11.1%) indicated that the degree of conversion of ester groups was 92%.

c. Preparation of isocyaniade derivative of poly(N-2-hydroxyethyl acrylamide)

1 g of poly(N-2-hydroxyethyl)acrylamide was dissolved in DMSO (90 ml). To this solution were added 10 ml of 0.05 solution of sodium-t-butoxide in DMSO, followed by 1.56 g of 1-tosyl-3-isocyano-propane, in 30 ml DMSO, pretreated with powdered KOH (final concentration of $Tos(CH_2)_3NC=0.05$ M). The reaction was allowed to continue at 30° for 1 hour, propan-2-ol (130 ml) was then added dropwise with stirring, followed by ether (250 ml). The fine swollen precipitate was separated on a sintered glass filter, redissolved in DMSO (90 ml) and reprecipitated with propan-2-ol and ether. The polymer was washed again with ether, dried in vacuo over $P_2O_5$, and stored in a closed vial over silica gel at $-15°$ C. Isocyanide content: 61 μmole/g (determined by binding of Gly-LeuNH$_2$).

EXAMPLE 9

Coupling of Enzyme to Isocyanide Derivatives of Cellulose

Isocyanide derivative of cellulose (50 mg powder) was suspended in 2 ml of a cold trypsin solution (10 mg protein) in 0.1 M sodium phosphate 0.5 M sodium acetate pH 8. Cold acetaldehyde (0.1 ml) was then added and the reaction allowed to proceed overnight with stirring at 4°. The insoluble enzyme derivative was separated by filtration, washed with water, 1 M KCl and again with water, resuspended in water (4 ml) and stirred at 4°.

The protein content of the cellulose-trypsin conjugate was 11.6 mg/gm support. (See Table I).

EXAMPLE 10

Coupling of Peptide to Isocyanide Derivatives of Cellulose

Isocyanide derivative of cellulose (30 mg powder) was suspended in 2 ml of an 0.1 M solution of glycyl-leucine amide in 0.1 M phosphate 0.5 M acetate containing 0.1 ml. acetaldehyde at pH 8.0. The reaction was allowed to proceed overnight with stirring at 4°.

The insoluble cellulose-gly-leu-NH$_2$ conjugate was separated by filtration, washed with water (500 ml) methanol, ether and air dried. The amount of bound peptide (25–30 moles 33 10$^{-6}$ gm) was determined by amino acid analysis of acid hydrolyzates of the cellulose derivative.

EXAMPLE 11

Coupling of Enzyme to Isocyanide Derivatives of Cross-Linked Dextran

Dried beads of the isocyanide derivative of the desired type of Sephadex (70 mg) were preswollen by suspension in the appropriate amount of dimethylsulfoxide (3 ml for G-75; 8 ml for G-150 and 10 ml for G-200) and stirred for 1 hr. at 30°. Ice-cooled water (30 ml) was added to the stirred suspension and the stirring continued for 5 min. (to ensure good mixing); the swollen polymer was separated by centrifugation, resuspended in cold water (35 ml), stirred for 5 min. spinned down, resuspended in cold 0.1 M phosphate 0.5 M acetate buffer pH 8.0 (35 ml), and spinned down again. The swollen precipitate was suspended in 0.1 M phosphate, 0.5 M acetate pH 8.0 to a total volume of 4 ml, for G-75, and 8 ml for G-150 and G-200. A weighed amount of trypsin (to bring the final concentration to 5 mg/ml) was added, followed by acetaldehyde (50 ml per ml). The reaction was allowed to proceed overnight with stirring at 4°; the enzyme-sephadex conjugate was separated on a sintered glass filter, washed with water, 1 M KCl and again with water and stored under water at 4°. The properties of the various Sephadex-trypsin conjugates are summarized in Table I.

EXAMPLE 12

Coupling of Peptide to Isocyanide Derivatives of Cross-Linked Dextran

Coupling of Gly Leu NH$_2$ to Sephadex was carried out essentially as described for the coupling of protein using an 0.1 M solution of peptide in the reaction mixture. The amounts of bound peptide are summarized in Table I and III.

EXAMPLE 13

Coupling of Enzyme to Isocyanide Derivatives of Cross-Linked Agarose

Trypsin was coupled to the isocyanide derivatives of CL-Sephrose 4B as described in Example 11 for Sephadex G-75 (see Table I).

EXAMPLE 14

Coupling of Peptide to Isocyanide Derivative of Cross-Linked Agarose

Glycyl-leucine amide was coupled to the isocyanide derivatives of CL-Sepharose 4B as described in example 12 for Sephadex G-75 (see Tables I and III).

TABLE I

Characterization of Isonitrile Derivatives of Polysaccharides

| Polysaccharide[a] | Bound Peptide[e] (μmole/gm) | Bound Enzyme[f] Total[g] (gm/mg conjugate) | Bound Enzyme[f] Active[h] (mg/gm conjugate) | % of total |
|---|---|---|---|---|
| Cellulose powder (230–270 mesh; 56–63 μm diameter) | 31[b] | 11.6 | 6.4 | 55 |
| Cross-linked Dextran (Sephadex) | | | | |
| G-75 | 19[b] | 8.8 | 8.8 | 100 |
| | 30[c] | 15.1 | 10.5 | 70 |
| G-150 | 12[b] | 12.7 | 8.8 | 70 |
| | 33[c] | 16.5 | 11.0 | 66 |
| G-200 | 12[b] | 15.7 | 12.3 | 78 |
| | 25[c] | 15.4 | 11.6 | 75 |
| Cross-linked Agarose (Sepharose-CL) 4B | 68[b] | 61.6 | 24.3 | 40 |
| | 91[c] | 91.3 | 28.5 | 30 |
| Linear Dextran (mol. wt. 250,000)[d] | 88[b] | 264 | 186 | 70 |
| Polyacrylamide[i] | 61 | 200 | 172 | 86 |

[a]Polysaccharide ionized by the addition of sodium-t-butoxide (500 μmole/gm polymer), followed by a 1-tosyl-3-isocyanopropane solution of the specified concentration (see footnotes [b] and [c]).
[b]Ionized polysaccharide treated with 0.05 M 1-tosyl-3-isocyanopropane.
[c]Ionized polysaccharide treated with 0.10 M 1-tosyl-3-isocyanopropane.
[d]Linear dextran dissolved in dimethylsulfoxide, ionized with sodium-t-butoxide and treated with 1-tosyl-3-isocyanopropane (0.05 M).
[e]Estimated from the leucine content of polysaccharide-gly-leu-NH$_2$ conjugates.
[f]Trypsin (EC.3.4.21.4).
[g]Determined by amino acid analysis of acid hydrolyzates of the appropriate polysaccharide-trypsin conjugate.
[h]Determined by rate assay (specific activity of native trypsin 33 esterase units/mg).
[i]Example 8

TABLE II

Preparation of Different Isonitrile Derivatives of Cellulose[a]

| Sodium t-butoxide[b] μmole/gm | Tos(CH$_2$)$_3$—NC[c] (M) | Isonitrile content[d] μmole/gm |
|---|---|---|
| — | 0.05 | — |
| 125 | 0.05 | 9.2 |
| 183 | 0.05 | 14.2 |
| 250 | 0.05 | 17.6 |
| 437 | 0.05 | 32.4 |
| 500 | 0.05 | 35.1 |
| 500 | — | — |
| 500 | 0.015 | 4.5 |
| 500 | 0.023 | 8.0 |
| 500 | 0.030 | 13.5 |
| 500 | 0.038 | 15.0 |
| 500 | 0.045 | 20.0 |
| 500 | 0.059 | 23.0 |
| 500 | 0.074 | 32.0 |

[a]Reaction mixture: 1 gm microcrystalline cellulose (56–63 μm diameter) in anhydrous dimethylsulfoxide and the appropriate amounts of sodium t-butoxide and 1-tosyl-3-isocyanopropane in total volume 45 ml.
[b]Added in the form of an 0.05 M solution in dimethylsulfoxide.
[c]Added in the form of an 0.1 M solution in dimethylsulfoxide (for details see experimental section).
[d]Determined titrimetrically

TABLE III

Preparation of Isonitrile Derivatives of Polysaccharides[a]

| Polysaccharides | Preswelling in dimethyl-sulfoxide (ml) | Sodium t-but-oxide (μmoles) | 1-tosyl-3-isocyanopropane | | | Total Volume or reaction mixture (ml) | Isocyanide content of modified polysac-charide[c] (μmole/gm) |
| | | | gms | Dissolved in dimethylsulfoxide (ml) | final concentration (M) | | |
|---|---|---|---|---|---|---|---|
| Cellulose powder 230-270 mesh (56-63 μm diameter) | 15 | 500 | 0.48 | 20 | 0.05 | 45 | 31 |
| Cross-linked Dextran (Sephadex) | | | | | | | |
| G-75 | 40 | 500 | 0.78 | 15 | 0.05 | 65 | 19 |
| | 40 | 500 | 1.56 | 15 | 0.10 | 65 | 30 |
| G-150 | 80 | 500 | 1.38 | 25 | 0.05 | 115 | 12 |
| | 80 | 500 | 3.12 | 40 | 0.10 | 130 | 33 |
| G-200 | 120 | 500 | 1.92 | 30 | 0.05 | 160 | 12 |
| | 120 | 500 | 4.32 | 50 | 0.10 | 180 | 15 |
| Cross-linked Agarose (Sepharose-CL) 2B | 70 | 500 | 1.20 | 20 | 0.05 | 100 | 64 |
| 4B | 70 | 500 | 1.20 | 20 | 0.05 | 100 | 63 |
| | 70 | 500 | 2.51 | 25 | 0.10 | 105 | 91 |
| Linear Dextran (mol. wt. 250,000) | 20[d] | 500 | 0.54 | 15 | 0.05 | 45 | 88 |

[a] All amounts given are for 1 gm polysaccharide. For details see experimental section.
[b] Added in the form of 0.05 M dimethylsulfoxide solution (10 ml).
[c] Estimated from the leucine content of polysaccharide-gly-leu-NH$_2$ conjugates.
[d] Linear dextran is dissolved in dimethylsulfoxide.

We claim:

1. An isocyano derivative of a linear or cross-linked polymer bearing a plurality of hydroxyl groups, said derivative having the general formula

P—O—Q—N≡C wherein P designates a polymeric backbone selected from the group consisting of cellulose, starch, linear dextran, cross-linked dextran, linear agarose, cross-linked agarose, polyvinyl alcohol and N-2-hydroxyethyl derivatives of a polyacrylamide, the oxygen atom is part of the hydroxy group, Q is a group —(CH$_2$)$_n$— wherein n is an integer of 3 to 20, said isocyano derivative containing from 9 to 100 micromoles (μ-mole) isonitrile groups per gram of said isocyano derivative.

2. An isocyano-substituted polymer according to claim 1, wherein Q designates a group —(CH$_2$)$_n$— wherein n is an integer from 3 to 12.

3. An isocyano substituted polysaccharide according to claim 1, wherein the polymer backbone is a cross-linked dextran, linear dextran, cross-linked agarose or linear agarose.

4. An isocyano substituted polymer according to claim 1, wherein the polymeric backbone is dextran or agarose.

5. An isocyano substituted polymer according to claim 4, wherein the polymeric backbone is dextran.

6. An isocyano substituted polymer according to claim 4, wherein the polymeric backbone is agarose.

7. A process for producing isocyano-substituted polyhydroxy linear or cross-linked polymer which comprises treating a polymer having hydroxy-groups with a strong base in a nonaqueous polar solvent so as to ionize the hydroxy-groups, reacting the ionized product with a compound of the formula X—Q—NC, wherein X is a good leaving group, Q is a —(CH$_2$)$_n$— group wherein n is an integer of 3 or more or an aralkyl moiety, resulting in a product of the formula P—O—Q—NC wherein P is the polymeric backbone, said polymeric backbone being selected from the group consisting of cellulose, starch, linear dextran, cross-linked dextran, linear agarose, cross-linked agarose, polyvinyl alcohol and N-2-hydroxyethyl derivatives of a polyacrylamide.

8. A process according to claim 7, wherein the nonaqueous polar aprotic solvent is dimethylsulfoxide.

9. A process according to claim 7, wherein the base used for ionization is t-butoxide.

10. A process according to claim 7, wherein the isocyanide is first contacted with a solid alkali metal hydroxide and subsequently reacted with the ionized polymeric material.

11. A process according to claim 7, wherein the isocyanide is of the formula Z—(CH$_2$)$_n$—NC wherein Z is a leaving group, n is an integer of 3 to 12, or wherein the isocyanide is 3-tosyl-1-isocyano propane.

* * * * *